United States Patent
Delaney (10) Patent No.: US 8,696,599 B2
(45) Date of Patent: Apr. 15, 2014

(54) MEDICAL SYSTEMS, DEVICES AND METHODS FOR COUPLING WIRE GUIDES

(75) Inventor: Kevin L. Delaney, Queensbury, NY (US)

(73) Assignee: Cook Medical Technologies LLC, Bloomington, IN (US)

( * ) Notice: Subject to any disclaimer, the term of this patent is extended or adjusted under 35 U.S.C. 154(b) by 451 days.

(21) Appl. No.: 12/680,710

(22) PCT Filed: Oct. 1, 2008

(86) PCT No.: PCT/US2008/078436
§ 371 (c)(1),
(2), (4) Date: Jul. 23, 2010

(87) PCT Pub. No.: WO2009/046097
PCT Pub. Date: Apr. 9, 2009

(65) Prior Publication Data
US 2010/0292614 A1    Nov. 18, 2010

Related U.S. Application Data

(60) Provisional application No. 60/976,922, filed on Oct. 2, 2007.

(51) Int. Cl.
*A61B 5/00* (2006.01)
(52) U.S. Cl.
USPC ......................................................... 600/585
(58) Field of Classification Search
USPC ......................................................... 600/585
See application file for complete search history.

(56) References Cited

U.S. PATENT DOCUMENTS

| | | | |
|---|---|---|---|
| 5,357,978 A | 10/1994 | Turk | |
| 5,609,627 A | 3/1997 | Goicoechea et al. | |
| 6,013,038 A * | 1/2000 | Pflueger | 600/585 |
| 6,156,016 A * | 12/2000 | Maginot | 604/264 |
| 6,254,610 B1 | 7/2001 | Darvish et al. | |
| 6,682,536 B2 | 1/2004 | Vardi et al. | |
| 6,884,258 B2 | 4/2005 | Vardi et al. | |
| 6,911,016 B2 * | 6/2005 | Balzum et al. | 604/95.04 |
| 6,939,368 B2 | 9/2005 | Simso | |
| 2002/0055733 A1 * | 5/2002 | Wilson | 604/528 |

(Continued)

FOREIGN PATENT DOCUMENTS

WO    WO 2007/001543 A1    1/2007

OTHER PUBLICATIONS

International Search Report/Written Opinion for PCT/US2008/078436 dated Jan. 14, 2009.

(Continued)

*Primary Examiner* — Brian Szmal
*Assistant Examiner* — H. Q. Nguyen
(74) *Attorney, Agent, or Firm* — Brinks Gilson & Lione (57) ABSTRACT

Medical systems, devices and methods are provided for coupling a wire guide to a previously introduced wire guide in intracorporeal procedures, and generally include a supplemental wire guide and a tracking element. The tracking element defines a first passageway and a second passageway. The first passageway is sized to receive the previously introduced wire guide and the second passageway is sized to receive the supplemental wire guide. The supplemental wire guide is attached to the tracking element in a coupled configuration and detached from the tracking element in a decoupled configuration for independent translation of the supplemental wire guide.

23 Claims, 4 Drawing Sheets

(56) References Cited

U.S. PATENT DOCUMENTS

| | | |
|---|---|---|
| 2003/0191491 A1 | 10/2003 | Duane et al. |
| 2004/0039372 A1 | 2/2004 | Carmody |
| 2004/0059291 A1 | 3/2004 | McDonnell et al. |
| 2004/0059369 A1 | 3/2004 | Duffy et al. |
| 2004/0122363 A1 | 6/2004 | Gribbons et al. |
| 2006/0259009 A1 | 11/2006 | Murray |
| 2007/0010863 A1* | 1/2007 | Stenzel .......................... 623/1.1 |

OTHER PUBLICATIONS

Preliminary Report on Patentability for PCT/US2008/078436 dated Apr. 15, 2010.

* cited by examiner

MEDICAL SYSTEMS, DEVICES AND METHODS FOR COUPLING WIRE GUIDES

CROSS REFERENCE TO RELATED APPLICATIONS

This application claims the benefit of priority to PCT/US08/078436 filed Oct. 1, 2008 which claims the benefit of Provisional Patent Application Ser. No. 60/976,922 filed Oct. 2, 2007, the entire contents of which are hereby incorporated herein by reference.

FIELD OF THE INVENTION

This invention relates generally to medical systems, devices and methods for using wire guides in intracorporeal procedures, and more particularly relates to coupling a wire guide to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005, and incorporated herein by reference.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

BRIEF SUMMARY OF THE INVENTION

The present invention provides medical systems, devices and methods for coupling a wire guide to a previously introduced wire guide in intracorporeal procedures, permitting easy and reliable placement of the supplemental wire guide, as well as allowing decoupling for independent translation of the supplemental wire guide.

One embodiment of a medical system, constructed in accordance with the teachings of the present invention, generally includes a supplemental wire guide and a tracking element. The supplemental wire guide has a main body and a distal end. The tracking element has a first portion defining a first passageway and a second portion defining a second passageway. The first passageway is sized to receive the previously introduced wire guide and permit translation of the tracking element relative to the previously introduced wire guide. The second passageway is sized to receive the supplemental wire guide. The medical system is operable between a coupled configuration and a decoupled configuration. The supplemental wire guide is attached to the tracking element in the coupled configuration such that translation of the supplemental wire guide causes translation of the tracking element. The supplemental wire guide is detached from the tracking element in the decoupled configuration for independent translation of the supplemental wire guide.

According to more detailed aspects, the tracking element is attached to a distal end of the supplemental wire guide in the coupled configuration. In one construction, the distal end of the supplemental wire guide includes a wound outer coil, and the second portion of the tracking element defines internal threads over at least a portion of the second passageway. The internal threads are sized and structured to matingly receive the wound outer coil of the distal end of the supplemental wire guide. A portion of the distal ends of the supplemental wire guide or the previously introduced wire guide may have an outer diameter greater than the diameter of the corresponding passageway to prevent translation of the tracking element beyond the distal end. The medical system may also include a tether connected to the tracking element for retraction thereof. In another construction, the main body of the supplemental wire guide may provide clearance with the second passageway to permit translation of a medical device over the supplemental wire guide and to the second passageway of the tracking element.

A method for coupling to a previously introduced wire guide during intracorporeal procedures is also provided in accordance with the teachings of the present invention. A medical system, such as the system described above, is provided in the coupled configuration. The previously introduced wire guide is positioned within the first passageway of the tracking element. The supplemental wire guide and tracking element are together translated distally along the previously introduced wire guide. The supplemental wire guide is decoupled from the tracking element, and is translated independently of the previously introduced wire guide. Depending on the construction of the medical system and device, the supplemental wire guide may remain within the second passageway of the tracking element, or may be outside of the second passageway. When a tether is employed, the method may also include retraction of the tether proximally to translate the tracking element over one or both of the two wire guides, either in the coupled configuration or decoupled configuration.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Turning now to the figures, FIGS. 1-5 depict a medical system 20 having a medical device 30 for coupling to a previously introduced wire guide 22 during intacorporeal procedures, in accordance with the teachings of the present invention. The previously introduced wire guide 22 generally includes a main body 24 having a distal end 26 with an end cap 28. The medical system 20 generally includes a supplemental wire guide 32 and a tracking element 34. The tracking element 34 is utilized to couple the supplemental wire guide 32 to the previously introduced wire guide 22 for simple and reliable introduction of the supplemental wire guide 32 along the path traversed by the previously introduced wire guide 22. At the same time, the medical system 20 and medical device 30 allow decoupling of the supplemental wire guide 32 so that it may be independently translated, thereby enabling a second path to be taken by the supplemental wire guide 32.

The supplemental wire guide 32 generally includes a main body 36 and a distal end 38. As best seen in the cross-sectional view of FIG. 2, the distal end 38 of the supplemental wire guide 32 is defined by a tapered distal end portion 36d of the main body 36, around which an outer wire 40 has been helically wound. As is known in the art, the tapered distal end portion 36d and outer wire 40 are joined through soldering or other mechanical means, including an end cap 42 formed at the distal tip of the supplemental wire guide 32. It will be recognized that the construction of the supplemental wire guide 32, as well as the previously introduced wire guide 22, may take numerous forms as many types of wire guides are known in the art, including solid wire, tubular wires, coiled wires and combinations thereof. For example, U.S. Pat. No. 5,243,996 discloses an exemplary solid wire mandrel having a coiled tip section, the disclosure of which is hereby incorporated by reference in its entirety.

Figure 4:
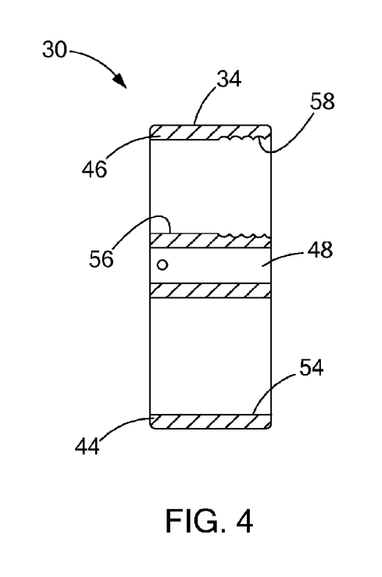
FIG. 4 is a cross-sectional view of the medical device depicted in FIGS. 1-3.
Figure 5:
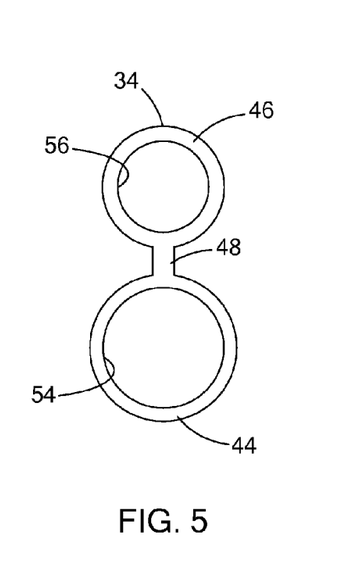
FIG. 5 is an end view of the medical device depicted in FIG. 4.

The tracking element 34 generally includes a first portion 44 and a second portion 46. The first portion 44 links the tracking element 34 to the previously introduced wire guide 22, while the second portion 46 links the tracking element 34 to the supplemental wire guide 32. As best seen in FIGS. 4 and 5, the first portion 44 of the tracking element 34 defines a first passageway 54, while the second portion 46 defines a second passageway 56. The first and second passageways 54, 56 have been shown as generally cylindrical, but they can take any cross-sectional shape as will be recognized by those skilled in the art. The second passageway 56 includes internal threads 58 extending along at least a portion of the length of the second passageway 56. The first passageway 54 is sized relative to an outer diameter of the previously introduced wire guide 22, and in particular its main body 24, to permit relative translation such that the tracking element 34 may slide along the previously introduced wire guide 22. Similarly, the second passageway 56 is sized relative to the supplemental wire guide 32, and in particular its main body 36, to permit relative translation such that the supplemental wire guide 32 may be at least partially slid through the second portion 46 of the tracking element 34.

A third portion 48 of the tracking element 34 connects the first and second portions 44, 46. An optional tether 50 such as a suture, cable, or wire is connected to the third portion 48, although it may be connected to any portion of the tracking element 34. The third portion 48 of the tracking element 34 preferably forms a hinge permitting relative movement between the first portion 44 and second portion 46 of the tracking element 34. That is, the third portion 48 may provide some flexure and is preferably formed as a living hinge. The ability for relative movement between the first and second portions 44, 46 can facilitate introduction and translation of the supplemental wire guide 32 along the previously introduced wire guide 22. The tracking element 34 preferably includes radiused or buffed outer edges to improve the atraumatic nature and facilitate translation of the tracking element 34 along the previously introduced wire guide 22. The tracking element 34 may be formed of various materials including metals such as stainless steel or platinum, alloys including super elastic alloys such a nitinol, various plastics such as polyvinylchloride, polyimide, polycarbonate, polyetherkeytone, or composites, and similar materials is known in the art.

Figure 1:
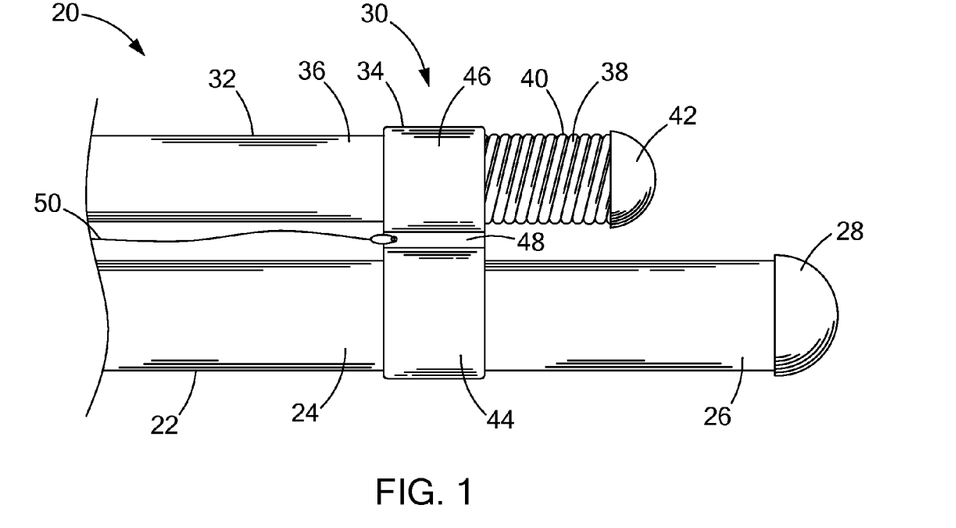
FIG. 1 is a side view of the medical system and medical device constructed in accordance with the teachings of the present invention.
Figure 2:
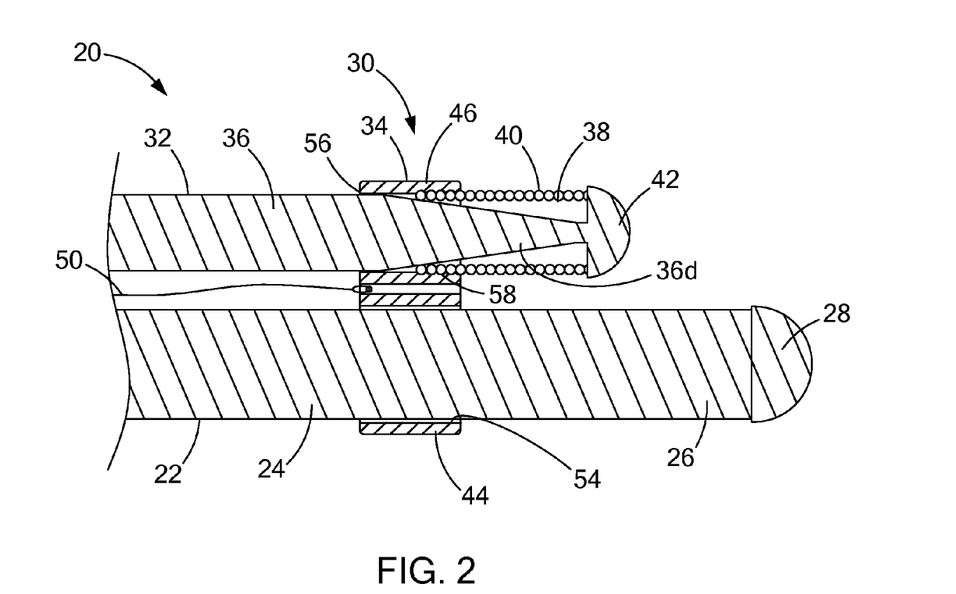
FIG. 2 is a cross-sectional view of the medical system and medical device depicted in FIG. 1.
Figure 3:
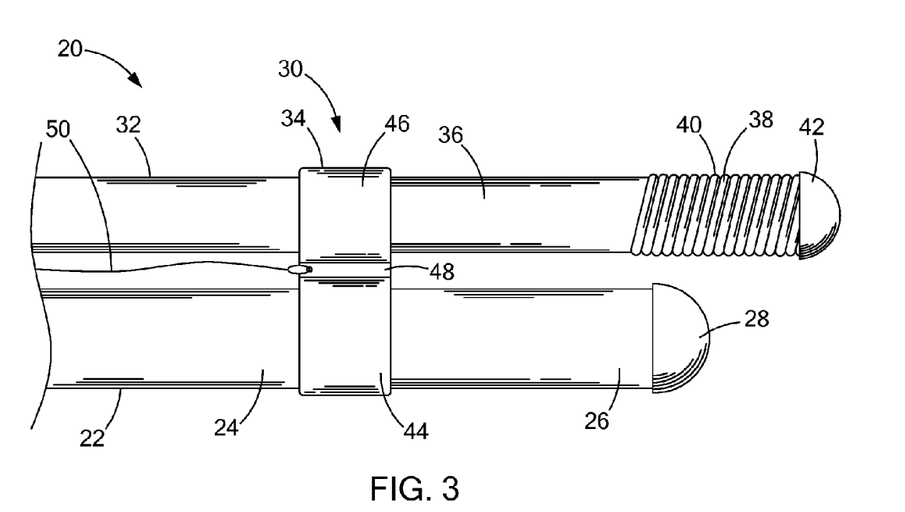
FIG. 3 is a side view of the medical system and medical device depicted in FIG. 1, depicting a decoupled configuration.

The medical system 20 is generally operable between a coupled configuration, as shown in FIG. 1, and a decoupled configuration, as is shown in FIG. 3. In the coupled configuration, the supplemental wire guide 32 is longitudinally attached to the tracking element 34 such that translation of the supplemental wire guide 32 causes translation of the tracking element 34. In the decoupled configuration, the supplemental wire guide 32 is longitudinally detached from the tracking element 34 for independent translation of the supplemental wire guide 32. More specifically, and as best seen in FIGS. 2 and 4, the internal threads 58 of the second portion 46 matingly receive the helically wound outer wire 40 in the coupled configuration. As such, the distal end 38 of the supplemental wire guide 32 is fixedly attached to the tracking element 34 for translation of the medical system 20 along the previously introduced wire guide 22. In the decoupled configuration, the supplemental wire guide 32 has been rotated or torqued such that the outer wire 40 no longer mates with the internal threads 58, whereby the supplemental wire guide 32 is detached from the tracking element 34. In this decoupled configuration, the main body 36 of the supplemental wire guide 32 may be freely translated through the second passageway 56, as shown in FIG. 3. In this manner, the supplemental wire guide 32 may be independently translated, for example, when it is desirable to take a second path during a medical procedure.

Depending upon the medical procedures to be performed, it may be desirable to prevent the tracking element 34 from passing beyond the distal end 26 of the previously introduced wire guide 22, and likewise beyond the distal end 38 of the supplemental wire guide 32. Accordingly, at least a portion of the distal ends 26, 38 can be sized larger than the first and second passageways 54, 56 of the tracking element 34. For example, the end cap 28 of the previously introduced wire guide 22 has been shown having an outer diameter greater than the first passageway 54, thereby preventing the tracking element 34 from passing beyond the distal end 26 of the supplemental wire guide 22. Likewise, the end cap 42 of the supplemental wire guide 32 has been shown as being larger than the second passageway 56 in the tracking element 34. On the other hand, either or both of the distal ends 26, 38 of the previously introduced wire guide 22 and supplemental wire guide 32 may alternatively be sized such that they can pass through the first and second passageways 54, 56 in the tracking element 34.

Figures 6, 7, 8:
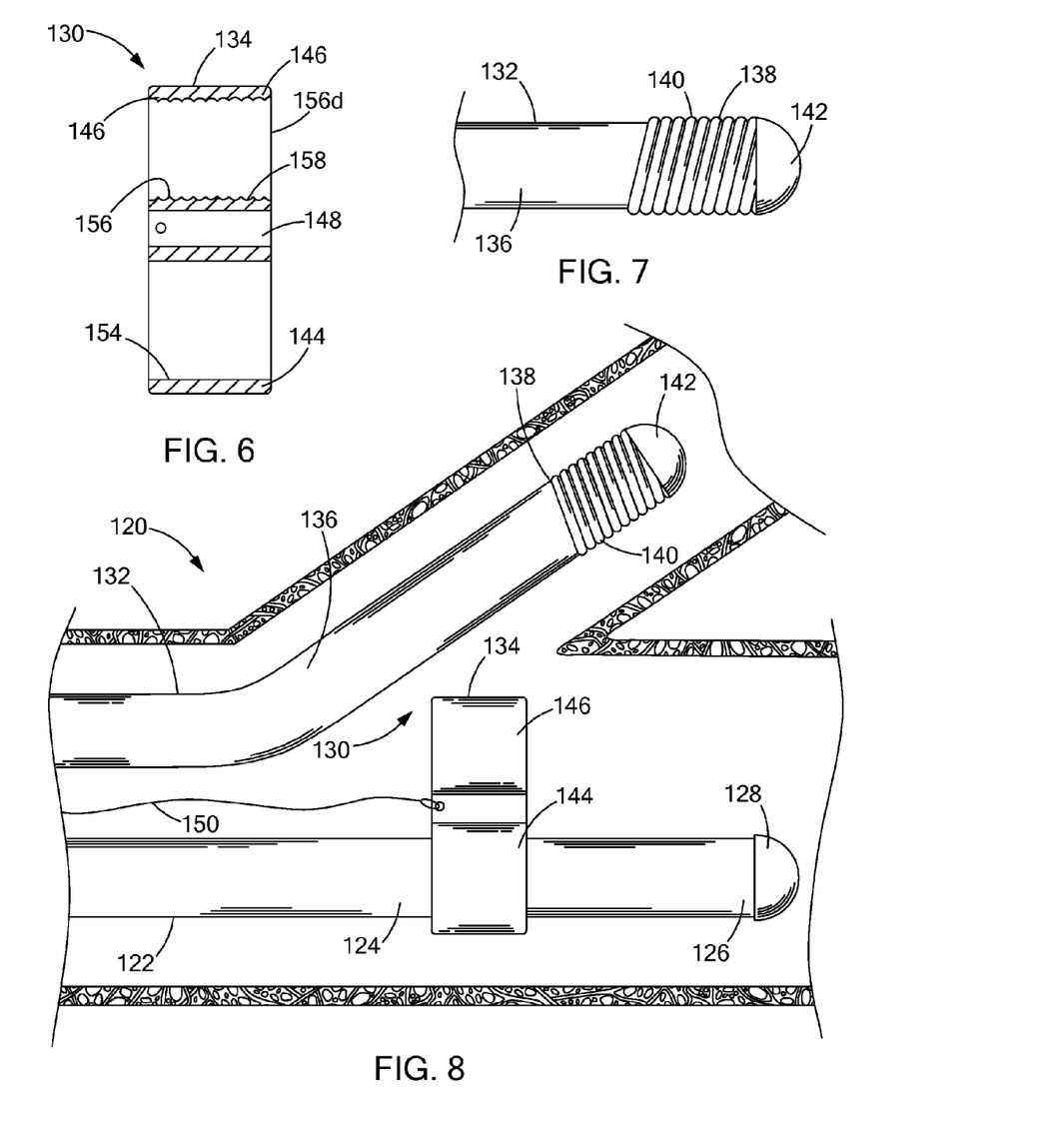
FIG. 6 is a cross-sectional view of an alternate embodiment of a medical device constructed in accordance with the teachings of the present invention.
FIG. 7 is a side view of an alternate embodiment of a supplemental wire guide forming a portion of the medical system.
FIG. 8 is a side view, partially in cross section, depicting the medical system and medical device of FIGS. 6 and 7 in a decoupled configuration.

As previously mentioned, the tether 50 can be employed and connected to the third portion 48 of the tracking element 34. Proximal retraction of the tether 50 permits the tracking element 34 to be withdrawn proximally once the supplemental wire guide 32 has assumed the decoupled configuration. Similarly, it may be desirable to completely remove the supplemental wire guide 32 from within the tracking element 34. For example, another embodiment of a medical system 120 and device 130 is shown in FIGS. 6-8 and includes a supplemental wire guide 132 having a main body 136 with a distal end 138 formed by an outer coiled wire 140 and an end cap 142. The tracking element 134 includes a first portion 144 and a second portion 146 connected by a third portion 148. The first portion 144 defines a first passageway 154 while the second portion 146 defines a second passageway 156. In this embodiment, internal threads 158 within the second portion 146 extend along the entire length of the second passageway 156. The end cap 142 of the supplemental wire guide 132 has an outer diameter sized less than or equal to an outer diameter defined by the outer wound wire 140 and the second passageway 156. In this manner, the supplemental wire guide 132 may be rotated to withdraw the supplemental wire guide 132 from the second passageway 158. In particular, the second passageway 156 includes a proximal port 156p and a distal port 156d, and the distal end 138 of the supplemental wire guide 132 may be retracted through the proximal port 156p such that the supplemental wire guide 132 does not extend through the second passageway 156. In this manner, and as shown in FIG. 8, the supplemental wire guide 132 may be independently translated, while the tracking element 134 remains linked to the previously introduced wire guide 122 (via the main body 124 extending through the first portion 144 of the tracking element 134).

Figure 9:
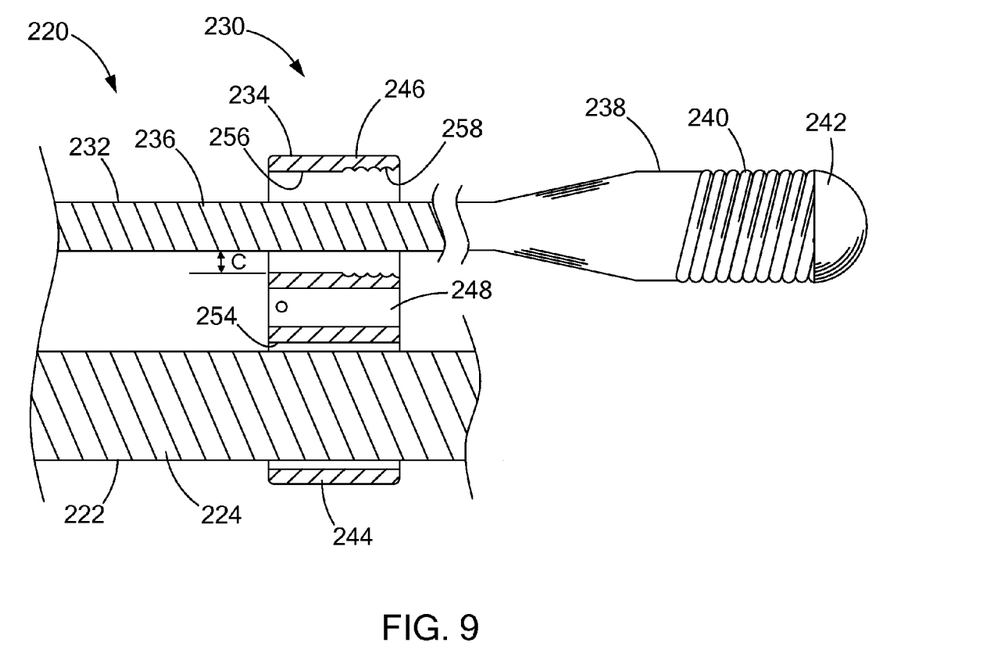
FIG. 9 is another embodiment of a medical system and medical device constructed in accordance with the teachings of the present invention.

It will also be recognized that in the embodiments of FIGS. 6-8, a catheter-based device such as a dilation balloon or the like may be passed over the supplemental wire guide 132, and when in the decoupled configuration, may be employed at a secondary location. Similarly, another embodiment of a medical system 220 and device 230 is shown in FIG. 9 and depicts how the passageway in the second portion of the tracking element can be sized relative to the supplemental wire guide to permit passage of catheter based devices therethrough. In particular, the tracking element 234 includes first, second and third portions 244, 246, 248 and defines a first passageway 254 and a second passageway 256. Here, the coupling wire 232 includes a main body 236 that does not taper at its distal end 238. An outer wire 240 is coiled around the distal end 238 and joins the main body 236 at a distal end cap 242. The main body 236 of the supplemental wire guide 232 has an outer diameter less than a diameter of the second passageway 256 to provide a clearance C therebetween. Preferably, the clearance C is sized to permit translation of a catheter-based medical device over the supplemental wire guide 232 and through the second passageway 256 of the second portion 246 of the tracking element 34.

A method employing these medical systems and medical devices is also provided in accordance with the teachings of the present invention. According to the method, a medical system, as such the medical systems 20, 120, 220 described above, is provided in the coupled configuration. Using the medical system 20 as an example, the previously introduced wire guide 22 is positioned within the first passageway 54 of the tracking element 34 such as by passing the tracking element 34 over the proximal end of the previously introduced wire guide 22. The supplemental wire guide 32 and tracking element 34 are together translated distally along the previously introduced wire guide 22. The supplemental wire 32 is decoupled from the tracking element 34, such as by rotating the proximal end (not shown) of the supplemental wire guide 32 to unscrew the coiled outer wire 40 from the internal threads 58 of the second passageway 56. The supplemental wire guide 32 is then translated independently of the previously introduced wire guide 22. The main body 36 of the supplemental wire guide 32 remains within the second passageway 56, although the main body 236 in the medical device 220 may be outside of the second passageway 256, as previously discussed. Likewise, when the medical device 30 includes a tether 50 connected to the third portion 58 of the tracking element 34, the tether 50 may be retracted to proximally translate the tracking element 34 over one or both of the two wire guides 22, 32, either in the coupled configuration or the decoupled configuration.

It will also be recognized by those skilled in the art that other mating structures may be formed to permit selective coupling and decoupling of the distal end of the supplemental wire guide and the tracking element. For example, flexible tabs and detents may be employed (such as the wire guide including outwardly extending tabs and the second passageway including corresponding detents) or other frictional fits or mechanical arrangements that may be overcome by either axial movement or rotational movement of the supplemental wire guide. Further, many different devices may be employed over either of the wire guides, including catheter devices, angioplasty devices, stenting devices, embolic protection devices, filtering devices, biopsy devices, cooling/aspiration devices and many other medical devices which may be tracked over a wire guide. Finally, while wire guides are often used in percutaneous interventional procedures, it will be recognized by those skilled in the art that the wire guide 20 of the present invention may also be employed non-percutaneously, such as in endoscopic or other intracorporeal procedures.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for coupling to a previously introduced wire guide during intracorporeal procedures, the medical system comprising:
   a supplemental wire guide having a main body and a distal end, the distal end including a wound outer coil;
   a tracking element configured to track over the previously introduced wire guide intracorporeally, the tracking element having a first portion and a second portion, the first portion defining a first passageway and the second portion defining a second passageway;
   the first passageway sized to receive the previously introduced wire guide therein and permit translation of the tracking element relative to the previously introduced wire guide;
   the second passageway sized to receive the supplemental wire guide, the second portion of the tracking element defining internal threads over at least a portion of the second passageway, the internal threads sized and structured to matingly receive the wound outer coil of the distal end of the supplemental wire guide; and
   the medical system operable between a coupled configuration and a decoupled configuration, the supplemental wire guide attached to the tracking element in the coupled configuration such that translation of the supplemental wire guide causes translation of the tracking element, the supplemental wire guide detached from the tracking element in the decoupled configuration for independent translation of the supplemental wire guide relative to the tracking element.

2. The medical system of claim 1, wherein a portion of the distal end of the supplemental wire guide has an outer diameter greater than a diameter of the second passageway.

3. The medical system of claim 2, wherein the distal end of the supplemental wire guide includes an end cap, and wherein an outer diameter of the end cap is greater than the diameter of the second passageway.

4. The medical system of claim 1, wherein the previously introduced wire guide has a distal end portion having an outer diameter, and wherein the outer diameter is greater than a diameter of the first passageway.

5. The medical system of claim 4, wherein the distal end portion of the previously introduced wire guide includes an end cap, and wherein the end cap has an outer diameter greater than a diameter of the first passageway.

6. The medical system of claim 1, further comprising a tether connected to the tracking element.

7. The medical system of claim 1, wherein the main body of the supplemental wire guide has an outer diameter less than a diameter of the second passageway to provide clearance therebetween.

8. The medical system of claim 7, wherein the clearance is sized to permit translation of a medical device over the supplemental wire guide and through the second passageway of the second portion of the tracking element.

9. The medical system of claim 1 wherein the second passageway includes a proximal port and a distal port, and wherein the supplemental wire guide may be attached to and detached from the tracking element at the distal port.

10. The medical system of claim 1, wherein the supplemental wire guide extends through the passageway to a distal side of the tracking element.

11. A medical device for coupling a supplemental wire guide with a previously introduced wire guide during intracorporeal procedures, the medical device comprising:
    a tracking element having a first portion and a second portion, the tracking element configured to track over the previously introduced wire guide intracorporeally;
    the first portion defining a first passageway extending through the tracking element; and
    the second portion defining a second passageway extending through the tracking element, the second passageway sized and structured for selective fixation to the supplemental wire guide at the distal port, the second passageway structured to matingly receive the supplemental wire guide, whereupon rotation of the supplemental wire guide the second passageway un-mates with the supplemental wire guide such that the supplemental wire guide is longitudinally detached from the tracking element for independent translation.

12. The medical device of claim 11, wherein the distal end of the supplemental wire guide includes a helically wound coil, and wherein the second portion of the tracking element defines internal threads over at least a portion of the second passageway, the internal threads sized and structured to matingly receive the helically wound coil of the distal end of the supplemental wire guide.

13. The medical device of claim 11, wherein the second portion of the tracking element defines internal threads over the entire length of the second passageway.

14. The medical device of claim 11, wherein the tracking element further includes a third portion connecting the first and second portions.

15. The medical device of claim 14, wherein the third portion defines a hinge permitting relative movement between the first and second portions of the tracking element.

16. The medical device of claim 11, further comprising a tether connected to the tracking element.

17. A method for coupling to a previously introduced wire guide during intracorporeal procedures, the method comprising:
    providing a medical system having a supplemental wire guide and a tracking element, tracking element including a first portion defining a first passageway and a second portion defining a second passageway, the first passageway sized to receive the previously introduced wire guide and permit translation of the tracking element relative to the previously introduced wire guide, the second passageway sized to receive the supplemental wire guide, the medical system operable between a coupled configuration and a decoupled configuration, the supplemental wire guide fixedly attached to the tracking element in the coupled configuration, the supplemental wire guide longitudinally detached from the tracking element in the decoupled configuration;

positioning the previously introduced wire guide within the first passageway;

translating the supplemental wire guide and tracking element together along the previously introduced wire guide intracorporeally;

decoupling the supplemental wire guide from the tracking element; and translating the supplemental wire guide independently of the previously introduced wire guide and the tracking element.

18. The method of claim 17, wherein the first passageway includes internal threads and the supplemental wire guide includes a coiled outer wire, and wherein the decoupling step includes rotating the supplemental wire guide relative to the tracking element.

19. The method of claim 17, wherein the second passageway includes a proximal port and a distal port, and wherein the decoupling step includes detaching the supplemental wire guide from the tracking element via the distal port such that the supplemental wire guide remains within the second passageway and is translatable relative thereto.

20. The medical system of claim 1, wherein the tracking element has a longitudinal length substantially shorter than a longitudinal length of the supplemental wire guide.

21. The medical system of claim 1, wherein the tracking element is structured such that, in the coupled configuration, distal translation of the supplemental wire guide causes distal translation of the tracking element over the previously introduced wire guide.

22. The medical system of claim 1, wherein the first and second passageways are parallel along their length.

23. The medical system of claim 1, wherein the coiled outer wire has a uniform outer diameter.

* * * * *

UNITED STATES PATENT AND TRADEMARK OFFICE
CERTIFICATE OF CORRECTION

PATENT NO. : 8,696,599 B2
APPLICATION NO. : 12/680710
DATED : April 15, 2014
INVENTOR(S) : Kevin L. Delaney It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 564 days.

Signed and Sealed this

Twenty-ninth Day of September, 2015

Michelle K. Lee
*Director of the United States Patent and Trademark Office*